US006676819B1

(12) United States Patent
Liu et al.

(10) Patent No.: US 6,676,819 B1
(45) Date of Patent: Jan. 13, 2004

(54) METHODS AND APPARATUS FOR AUTOMATIC ON-LINE MULTI-DIMENSIONAL ELECTROPHORESIS

(76) Inventors: Yaoqing Diana Liu, 1015 Cadillac Way, Apt. 316, Burlingame, CA (US) 94010-2542; James Jianmin Bao, 1015 Cadillac Way, Apt. 316, Burlingame, CA (US) 94010-2542

( * ) Notice: Subject to any disclaimer, the term of this patent is extended or adjusted under 35 U.S.C. 154(b) by 275 days.

(21) Appl. No.: 09/659,420

(22) Filed: Sep. 11, 2000

Related U.S. Application Data
(60) Provisional application No. 60/153,660, filed on Sep. 14, 1999.

(51) Int. Cl.[7] .......................... B01D 57/02; B01D 59/42; B01D 59/50; B01D 61/42; B01D 61/58; C02F 1/469; C07K 1/26; C08F 2/58
(52) U.S. Cl. .................... 204/451; 204/452; 204/453; 204/604; 73/863.31; 73/863.32; 73/864.21; 73/864.22
(58) Field of Search .................... 204/451, 450, 204/452–453, 604; 73/863.31, 863.32, 864.21, 864.22

(56) References Cited

U.S. PATENT DOCUMENTS

| | | | | |
|---|---|---|---|---|
| 5,439,578 A | * | 8/1995 | Dovichi et al. | 204/603 |
| 5,968,331 A | * | 10/1999 | Kambara et al. | 204/450 |
| 6,007,690 A | * | 12/1999 | Nelson et al. | 204/601 |
| 6,103,083 A | * | 8/2000 | Merenkova et al. | 204/452 |
| 6,103,199 A | * | 8/2000 | Bjornson et al. | 204/450 |
| 6,132,582 A | * | 10/2000 | King et al. | 204/453 |
| 6,143,152 A | * | 11/2000 | Simpson et al. | 204/451 |
| 6,482,364 B2 | * | 11/2002 | Parce et al. | 422/100 |

\* cited by examiner

Primary Examiner—Mark L. Bell
Assistant Examiner—Jennine Brown

(57) ABSTRACT

The invention provides a method of performing one- and two-dimensional electrophoresis with or without gel in an automated way. The two dimensional electrophoresis can be performed either separately or continuously. Both electrokinetic and hydrodynamic forces can be used to facilitate sample transfer from the first to the second dimension. The samples can be detected on-line by using common detectors like UV-Vis, laser induced fluorescence (LIF), and mass spectrometry (MS).

30 Claims, 12 Drawing Sheets

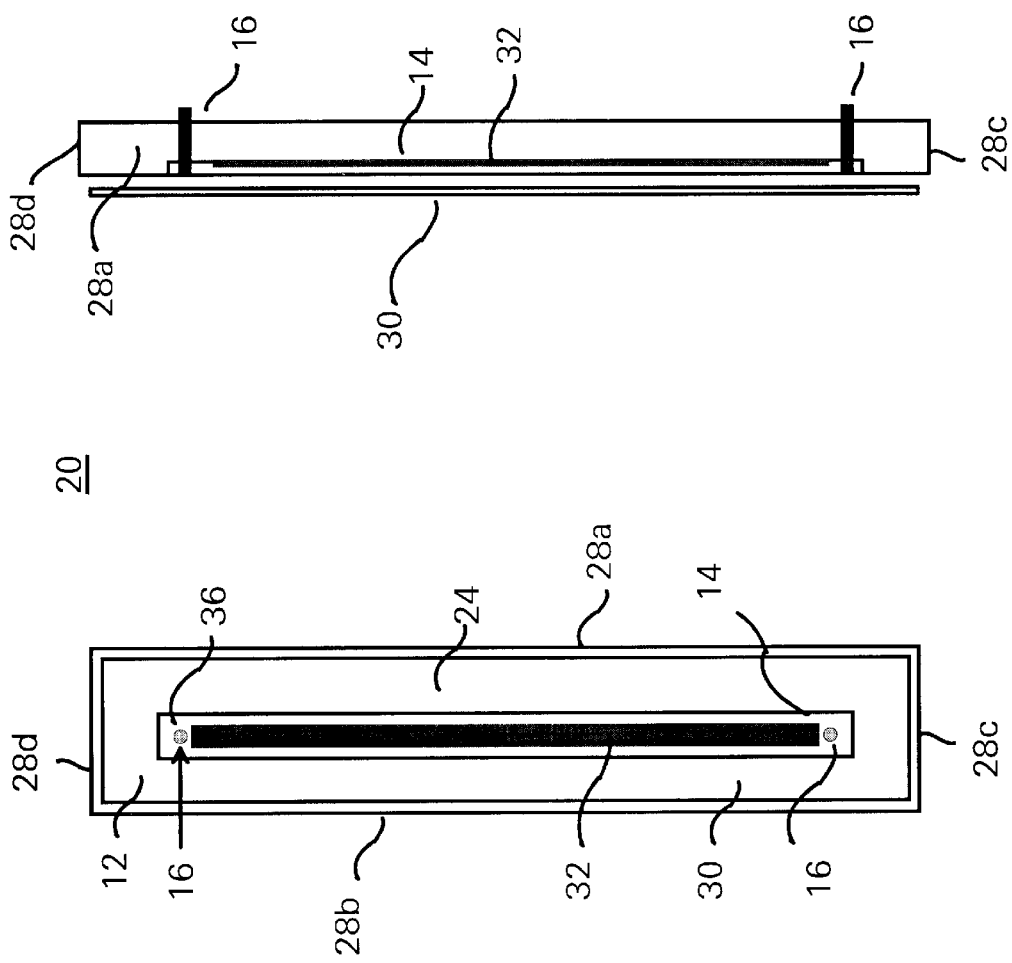

METHODS AND APPARATUS FOR AUTOMATIC ON-LINE MULTI-DIMENSIONAL ELECTROPHORESIS

CROSS-REFERENCE TO RELATED APPLICATIONS

This application claims the benefit of U.S. Provisional Application Serial No: 60/153,660 entitled "Method and apparatus for interfacing multi-dimensional electrophoresis for automatic on-line analysis" filed on Sep. 14, 1999. This application is incorporated herein by reference.

REFERENCES CITED

U.S. PATENT DOCUMENTS

| | | | |
|---|---|---|---|
| 5,571,398 | November, 1996 | Karger | 204/603 |
| 5,582,705 | December, 1996 | Yeung et al. | 204/605 X |
| 5,858,194 | January, 1999 | Bell | 204/601 |
| 5,872,010 | February, 1999 | Karger | 436/173 |
| 5,888,363 | March, 1999 | Abubaker | 204/452 |
| 5,938,908 | August, 1999 | Anazawa | 204/603 |
| 6,048,444 | April, 2000 | Takahashi | 204/603 |
| 6,048,498 | April, 2000 | Kennedy | 204/603 |
| 6,063,251 | May, 2000 | Kane | 204/603 |
| 6,103,083 | August, 2000 | Merenkova | 204/603 |

STATEMENT REGARDING FEDERALLY SPONSORED RESEARCH OR DEVELOPMENT

Not Applicable

BACKGROUND OF THE INVENTION

The present invention relates to interfacing two-dimensional electrophoretic separations of biomolecules, such as protein, DNA, and carbohydrates involving capillary electrophoresis (CE). Specifically, the present invention relates to interfacing multiple capillaries either fabricated on a microchip or bundled together with multiple individual capillaries as in capillary array electrophoresis (CAE) with a different channel (capillary and/or strip gel) perpendicularly to provide sample transfer to multiple capillaries simultaneously.

Usually, electrophoresis separates protein mixtures based either on their charges or on their sizes (molecular weights). By combining these two mechanisms, which are orthogonal to each other, a particularly powerful tool called two-dimensional polyacrylamide gel electrophoresis (2-D PAGE) is formed (Kenrick, K. G. and Margolis, J. Isoelectric focusing and gradient gel electrophoresis: a two-dimensional technique, Anal. Biochem. 1970, 204–207; O'Farrell, P. H. High resolution two-dimensional electrophoresis of proteins, J. Biol. Chem. 1975, 250, 4007–4021). The modern two-dimensional electrophoresis has improved significantly with many modifications to the original technique developed almost thirty years ago. However, the general procedures remain the same, typically involving sequential separations by first dimension of isoelectric focusing (IEF) and the second dimension of slab gel electrophoresis (SGE) using sodium dodecyl sulphate (SDS).

This 2-D PAGE technology is the only technique known so far capable of separating thousands of proteins simultaneously and providing highly purified proteins. Actually, 2-D PAGE is the core technology that forms the basis for the rapid expanding field of proteomics and genomics (Wilkins, M. R., Williams, K. L., Appel, R. D. and Hochstrasser, D. F., Eds, Proteome Research: New frontiers in Functional Genomics, Springer, Berlin, 1997). Currently, proteomics and genomics heavily rely on 2-D PAGE and related technologies to separate, identify and quantitate proteins. Unfortunately, the current 2-D PAGE technique requires separate steps and is very hard to automate. Therefore, it is critical for the future development of proteomics to automate the protein separation and quantitation process. To date, very few successful results have been reported for the automation of 2-D PAGE.

Recently, capillary electrophoresis (CE) has emerged as a powerful separations technique, with applicability toward a wide range of molecules from simple atomic ions to large DNA fragments. In particular, two of the operational modes, i.e. capillary IEF (cIEF) and capillary gel electrophoresis (CGE), have become attractive alternatives to slab gel electrophoresis for biomolecule analysis, including protein separation and DNA sequencing. This is generally attributed to the fact that the small size of the capillary greatly reduces Joule heating associated with the applied electrical potential. Furthermore, cIEF and CGE produce faster separation with better resolution than slab gels. Especially, the sub-nanoliter sample volume requirement make these technique extremely attractive for biomedical analysis where samples are often too hard to get enough for other techniques to work. Because of the sub-nanoliter size of the samples involved, however, a challenging problem in applying this technology is to handling the samples including transferring the samples from one dimension to another.

ISOELECTRIC FOCUSING

Isoelectric focusing separation of proteins in an immobilized pH gradient (IPG) is extensively described in the art. The concept of the immobilized pH gradient (IPG) is disclosed in U.S. Pat. No. 4,130,470 and is further described in numerous publications (Bjellqvist, B., Ek, K., Postel, W., Isoelectric focusing in immobilized pH gradients: principle, methodology, and some applications, *J Biochem. Biophys. Methods* 1982, 6,317–339; Gorg, A. Postel, W., Gunther, S., Weser, J., Improved horizontal two-dimensional electrophoreis with hybrid isoelectric focusing in immobilized pH gradients in the first dimension and laying-on transfer to the second dimension, *Electrophoresis*, 1985, 6,599–604).

It is current practice to create IPG gels in a thin planar configuration bonded to an inert plastic sheet that has been treated for chemical binding to an acrylamide gel. The IPG gel is typically formed as a rectangular plate of 0.5 mm thick, 10 to 30 cm long (in the direction of separation) and about 10 cm wide. Multiple samples can be applied to such a gel in parallel lanes, with the attendant problem of diffusion of proteins between lanes producing cross contamination. In the case where it is important that all applied protein in a given lane is recovered in that lane (as is typically the case in 2-D electrophoresis), it has proven necessary to split the gel into narrow strips, (Immobiline DryStrips, typically 3 mm wide), each of which can then be run as a separate gel. Since the protein of a sample is then confined to the volume of the gel represented by the single strip, it will all be recovered in that strip.

IEF can also be performed in capillaries (Hjerten, S., Zhu, M. D., Adaptation of the equipment for high-performance electrophoresis to isoelectric focusing, *J. Chromatogr*. 1985, 346, 265–70; Hjerten, S., Liao, J. L, Rapid separation of proteins by isoelectric focusing in the high-performance electrophoresis apparatus, *Protides Biol. Fluid*. 1986, 34, 727–30; Thormann, W., Tsai, A., Michaud, J. P., Mosher, R.

A., Bier, M., *J. Chromatogr.* 1987, 389, 75–86). In cIEF, the pH gradient is usually provided by supplying the full capillary with a mixture of the heterogeneous ampholytes and the homogeneous separation medium along with protein samples. The current cIEF suffers from two major limitations. One is the detection of the separated proteins bands. Since the whole content is restricted within the capillary, a solution with either high salt concentration or extreme pH has to be used to elute the analytes out from one of the capillary end for detection. Recently, some work to image the whole capillary for the separated bands have been reported (Fang, X., Tragas, C., Wu, J., Mao, Q., Pawliszyn, J., Recent development in capillary electric focusing with whole column imaging detection, *Electrophoresis*, 1998, 19, 2290–2295). The second limitation is the difficult to create the equivalent of IPG strips in the capillary due to geometric restriction (Hochstrasser, D., Augsburger, V., Funk, M., Appel, R., Pellegrini, C., Muller, A. F., Immobilized pH gradients in capillary tubes and two-dimensional gel electrophoresis, *Electrophoresis*, 1986, 7, 505–11). Therefore, the whole buffer system migrates, due to electroosmotic flow, during the IEF process making the focusing process difficult to reproduce. Coating the capillary surfaces with a hydrophilic layer reduces the electroosmosis and thus the buffer migration process (Bao, J., Separation of proteins by capillary electrophoresis using an epoxy based hydrophilic coating, J. Liq. Chrom. & Rel. Technol., 2000, 23, 61–78). However, most of the coatings cannot resist the extreme pHs involved in the IEF process for long. Fortunately, most of the cIEF can be accomplished within a shorter period of time due to a much higher voltage in cIEF as compared with traditional IEF process. Therefore, cIEF is still a very practical technology for protein separations.

Further, cIEF can also be performed on microchips. The details of this art have been described in details in references (Dolnik, V., Liu, S., and Jovanovich, S., Capillary electrophoresis on microchip, *Electrophoresis* 2000, 21, 41–54).

SDS-PAGE

The principle and practices of SDS-PAGE are also extensively described in the art. It is current practice to detect proteins in SDS-PAGE gels either by staining the gels or by exposing the gels to a radiosensitive film or plate (in the case of radioactively labeled proteins). Staining methods include dye-binding (e.g., Coomassie Brilliant Blue), silver stains (in which silver grains are formed in protein-containing zones), negative stains in which, for example, SDS is precipitated by Zn ions in regions where protein is absent, or the proteins may be fluorescently labeled. In each case, scanners can be used to acquire the spot pattern images of the separated proteins. The images can be reduced to provide positional and quantitative information on sample protein composition through the action of suitable computer software. All of these detection techniques have their limitations, especially in terms of quantitation. Better method is desirable.

SDS-PAGE can also be performed in capillaries. Capillary SDS-PAGE has demonstrated its power in protein separation (Cohen, A. S., Karger, B. L, *J. Chromatogr.* 1987, 387, 409) as well as in DNA separation (Yeung, E. S., Li, Q., DNA sequencing by multiplexed capillary electrophoresis, in *High Performance Capillary Electrophoresis*, edited by Morteza G. Khaledi, Chemical Analysis Series, *Vol.* 146, 1998, John Wiley & Sons, pp 767–89). Capillary SDS-PAGE has many unique advantages such as easiness for detection and quantitation. When used for protein separation, all known on-line detection techniques for capillary electrophoresis (CE), such as WV-Vis, LIF (laser induced fluorescence) and MS detection can be used for the quantitation of the proteins. This feature is critical for providing quantitative information about the proteins being separated. Therefore, it is advantageous to use capillary SDS-PAGE for final protein determination.

Both IEF and SDS-PAGE have played important roles in advancing modern biology and chemistry. However, pharmaceutical companies facing strong competition and regulatory pressure are designing more and more experiments, which result in large numbers of samples for evaluation. The conventional slab gel based electrophoresis and single capillary-based CE cannot meet the ever-demanding need for sample throughput. One solution is to conduct analysis of multiple samples simultaneously in many capillaries bundled together, i.e., multiplexed simultaneously order to same time and reduce cost. For example, attempts have been made to sequence DNA in slab gels with multiple lanes to achieve multiplexing. However, slab gels are not readily amenable to a high degree of multiplexing and automation. Difficulties exist in preparing uniform gels over a large area, maintaining reproducibility over different gels, and loading sample wells. Furthermore, difficulties arise as a result of the large physical size of the medium, which requires a uniform cooling, large amounts of media, buffer, and samples, and long run times for extended reading of nucleotides. However, capillary electrophoresis can be highly multiplexed and run in parallel. The substantial reduction of Joule heating per lane makes the overall cooling and electrical requirement more manageable. The cost of materials per lane is reduced because of the smaller sample sizes. Therefore, the advantages of CE can produce substantial gain in shortening the time needed for various sample assays.

TWO-DIMENSIONAL ELECTROPHORESIS

Both IEF and SDS-PAGE have proven to be important separation techniques. Further, they can be combined together to form a two-dimensional electrophoresis (2-D PAGE) system and to give more separation power as they are orthogonal separation techniques, which means that the separation parameter for SDS-PAGE, mass, is almost completely unrelated to the separation parameter of IEF (pI). The theoretical resolution of the 2-D system is the product of the resolutions of each of the constituent methods, which is in the range of 150 molecular species for both IEF and SDS electrophoresis. This gives a theoretical resolution for the complete system of 22,500 proteins, which accounts for the intense interest in this method. In practice, 5,000 proteins have been successfully resolved experimentally.

Two-dimensional electrophoresis is widely used to separate from hundreds to thousands of proteins in a single analysis, in order to visualize and quantitate the protein composition of biological samples such as blood plasma, tissues, cultured cells, etc. The technique was introduced in 1975 by O'Farrell, and has been used since then in various forms in many laboratories (O'Farrell, P. H., High resolution two-dimensional electrophoresis of proteins, *J. Biol. Chem.* 1975, 250, 4007–4021; Klose, J., Protein mapping by combined isoelectric focusing and electrophoresis of mouse tissues; A navel approach to testing for induced point mutation in mammals, *Humangenetik*, 1975, 26, 231–243; Scheele, G. A., Two-dimensional gel analysis of soluble proteins: characterization of guinea pig exocrine pancreatic proteins, *J. Biol. Chem.* 1975, 250, 5375–5385). Even today, 2-D PAGE is still the only known technique capable of separating thousands of proteins in complex samples.

(Herbert, B. R., Sanchez, J. C. and Bini, L., Two-dimensional electrophoresis: the state of the art and future directions, in Proteome Research: new frontiers in functional genomics, Wilkins, M. R., Williams, K. L., Appel, R. D., and Hochstrasser, D. F. Eds. pp13–34, 1997). Because 2D-PAGE has the ability to provide detailed views of thousands of proteins expressed organism or cell type, it has undeniably assumed a major role in protein separation and identification (Cash, P., *Anal. Chim. Acta*, 1998, 372, 121–145).

The key to the success of 2-D PAGE is to have a proper way of transferring proteins separated by IEF into the second dimension. The transfer of biopolymers, such as proteins, DNA and RNA from free solution is relatively straightforward. But, transferring biopolymers from gels is problematic due to the physical barriers that the large molecules encounter. Usually, the biopolymers are well enmeshed inside the gel and can be released only after being coaxed strongly. Several methods have been used for recovering biopolymers from a gel. These methods include direct extraction, sonication, electroblotting, electroelution, and electrophoresis.

4. Extraction method is to directly cut out the gel with the band of interest, mash it and immerse it in a buffer solution containing SDS, glycine and Tris((tris-hydroxymethyl)-aminomethane). After shaking the mixture and filtering out the gels, the protein is recovered by extraction. This method is highly unsatisfactory for large proteins because large proteins diffuse very slowly within the complex gel network.

5. Sonication increases the rate of protein diffusion from within the pores of the gel out into the solvent. But, the efficiency is still low and the process takes a long time. In addition, excessive sonication may result in the degradation of the sample molecules.

6. Electroblotting, the most common and satisfactory method of recovering proteins, involves transfer of proteins from the gel onto another equally sized nitrocellulose membrane, using an electric current to drive their migration in a manner similar to the original electrophoresis, but in a perpendicular direction (Western blot). The reason for performing an electroblot is that the proteins are now more accessible on the transfer membrane than they were in the gel. For instance, detection techniques are more sensitive and the proteins on the membrane can be reacted in situ, with antibodies or other agents.

7. Electroelution is another commonly used method of recovering sample from gel. In this method, gel containing the nucleic acid of interest is cut out and put into a dialysis bag filled with buffer. After the gel has sunk to the bottom of the bag, the excess buffer is removed. The bag is then immersed in a shallow tank of buffer and electric current is passed through the bag. The nucleic acid is then electroeluted onto the wall of the bag. The polarity of the current is reversed for a short time to release the nucleic acid from the wall of the bag. The nucleic acid is thereby recovered and purified.

8. Electrophoresis is the best method for recovering samples from the gel. In a 2-D PAGE, proteins from the IEF gel is easily transferred to the SDS-PAGE gel by electrophoresis. After the IEF step, the IEF gel strip containing proteins separated by IEF is taken out of the IEF chamber and placed along the edge of the SDS-PAGE gel with the SDS-PAGE process in a direction perpendicular to the prior IEF separation. Protein molecules are transferred to the SDS-PAGE gel during the electrophoresis process to yield a two-dimensional (2-D) separation. This interface is the best approach available so far to transfer protein molecules from the IEF step to the SDS-PAGE step because it provides a seamless transition of proteins from the IEF gel to the SDS-PAGE gel. This is no surprise as electrophoresis is the most effective means of moving biopolymers in gel. The only drawback of this interface is that manual operation is required to take the IPG strip out and place it along the SDS-PAGE gel in order to complete the process. This manual procedure makes it difficult for automation of the whole process.

Moreover, the current IPG and slab gel systems are not fully automated, wherein all operations including gel casting, processing, sample loading, running and final disposition are carried out by an integrated, fully automated system. Current gel systems cannot be fully controlled by a computer and cannot systematically vary gel, process, sample load and run parameters, provide positive sample identification, and cannot collect process data with the object of optimizing the reproducibility and resolution of the protein separations. The current invention takes advantage of the electrophoresis principle and used capillary electrophoresis as a means of transferring the samples electrically into a capillary for convenient detection and analysis.

Several references in the literature describe the coupling of slab gel electrophoresis to mass spectrometry for protein characterizations (Busch, K. L, Interface device and process to couple planar electrophoresis with spectroscopic methods of detection, U.S. Pat. No. 5,245,185, Sep. 14, 1993.). This is a fundamentally different form of coupling (electrophoresis to mass coupling) and is not considered relevant to the present invention (electrophoresis to electrophoresis).

Capillary IEF can also be interfaced with different techniques through its outlet end. For example, MS has been used to interface with cIEF technique for protein analysis (Tang, Q., Harrata, A. K., Lee, C. S., Capillary isoelectric focusing-electrospray mass spectrometry for protein analysis, *Anal. Chem.* 1995, 67, 3515–19). In addition, there have been many reports attempting to interface HPLC with other electrophoretic techniques (Hanash, S. M.; Strahler, J. R. Advances in two-dimensional electrophoresis, *Nature (London)*, 1989, 337, 485–6; Snider, J., Neville, C., Yuan, L. C., Bullock, J., Characterization of the heterogeneity of polyethylene glycol-modified superoxide dismutase by chromatographic and electrophoretic techniques, *J. Chromatogr.* 1992, 599, 141–55; Hooker, T. F., Jeffery, D. J., and Jorgenson, J. W., Two-dimensional separations in high-performance capillary electrophoresis, in *High Performance Capillary Electrophoresis*, edited by Morteza G. Khaledi, Chemical Analysis Series, Vol. 146, 1998, John Wiley & Sons, pp 581–612; Jorgenson, J. W. and Lemmo, A. V., U.S. Pat. No. 5,496,460). Further, cIEF has even been interfaced with traditional gel electrophoresis (Hirota, M., Development of a new type of two-dimensional electrophoresis and its application to the analysis of alkaline phosphatase isoenzymes in sera of pregnant woman, *Yamaguchi Igaku* 1986, 35, 87–95). However, this kind of interface still requires the move of proteins out of one end of the capillary, which is different from the current invention. Therefore, there has been no report on interfacing cIEF with multiplexed capillary array electrophoresis process. Especially, there is no report for interfacing cIEF perpendicularly with other techniques including SDS-PAGE. Further, there is no report for interfacing multiplexed capillary with another capillary array systems.

OBJECT OF INVENTION

The present invention is aimed primarily at providing a means and a system for interfacing the multiplexed capillaries to different channels (or capillaries or gel strips) for the 2-D applications, and providing means for automating the whole 2-D process to afford higher throughput, resolution, speed, and automation.

It is an object of the present invention to provide a system for use in a 2-D system using all known methodologies associated with single capillary cIEF including sampling, detection, and elution.

It is a further object of the present invention to provide a cIEF system using all known methodologies associated with ultra thin EPG strips for cIEF.

It is a further object of the present invention to provide a multiplexed capillary array system for SDS-PAGE as second dimension in a 2-D process utilizing all known methodologies associated with single capillary SDS-PAGE including sampling, run parameters, detection and buffer selection.

SUMMARY OF THE INVENTION

The present invention provides an apparatus and a means for interfacing multiplexed CE capillaries with a channel that is used for conducting another dimension of separation. The apparatus is consisted of a channel, a substrate, a cover, and an interface.

A channel according to the present invention includes an opening disposed in a substantially planar substrate with a proper cover and at least one end opening of the channel is in fluid communication with external fluid through either a hole on the cover or the side surface of the substrate. If the channel openings extend through the side surface of the substrate, the channel opening can be manufactured simultaneously with the channel in the planar surface of the substrate. Thus, there is no need for specially drilled ports that must be aligned with the tiny channels from the sides. In this case, the channel should be fabricated to the edge of the substrate for connection with external capillaries. If the end opening is extended toward the reagent reservoirs on the outer surface, the whole channel is fabricated within the substrate and fluid communication is achieved through the hole on the cover. Preferred channel embodiments include at least a second channel opening that is coplanar with the first channel opening. The channel is suitable for transporting a sample during CE process.

Each channel can include a network of interconnected channels, if necessary, and each channel can include an opening that extends through one of the side surfaces of the substrate or an alternate surface of the substrate. For example, a plurality of channel openings can extend through the same surface to facilitate interaction with the interface as described below. Additionally, groups of channel openings can be spaced apart with certain distance on the substrate.

A substrate is used to house the channel. Various substrates ranging from glass to plastics can be used as the substrate. Channels can be made using different techniques available for different substrates. For example, molding or ablation can be used to fabricate channels on plastics. If silicone rubber is used as the substrate, a simple casting can be done with on a proper mold to generate the channels.

A cover can be made of different materials including glass and rubber and is used to cover the surface of the substrate with channels fabricated on it. If glass is used, there is only one way, i.e. from the side surface between the cover and the substrate, for interfacing capillary array with the channel. For rubber cover, in addition to the side surface, the interface can be accomplished from the front surface. This cover serves multiple purposes. First, it covers the channels fabricated on the substrate to form a capillary, through which CE process can be performed. Second, holes can be drilled on it to serve as reagent reservoirs to supply fluid to the capillary on the substrate. Third, electrodes can be placed in the reservoirs to provide electric contact for the capillary. Fourth, if the interface with capillary array is conducted through the outer surface (for rubber cover only), this cover sheet serves as an interface for capillary needles to insert in.

An interface having features of the present invention is useful for interfacing a channel having a pair of spaced apart channel end openings with externally applied fluids. In alternative embodiments the interface includes a capillary area, a conductor area, and an ionic fluid disposed in reagent reservoirs for establishing an electrical path between the channel area and the electrode. The ionic fluid is disposed in at least a portion of each end to establish the electrical path between the channel area and the conductor area. The ionic fluid can be the sample being tested or an alternate fluid, such as a separation buffer or other reactant.

The invention also includes a method for making a channel and a method for interfacing a channel opening with an electrical conductor and reactant fluids. Wherein the first dimension of separation, either electrophoretic (i.e., IEF or zone electrophoresis) or chromatographic, can be performed without interruption while the second dimension of CE separation can be run independently.

This multiplexing approach involves inserting a bundle of capillaries that are coupled individually in a capillary array or are fabricated in a microchip. The coupling can be done by inserting at least one capillary of the capillary array into the first dimension of separation channel that contains sample. It can also be accomplished by placing the tips of the capillary array adjacent to and perpendicular in relation to the first separation channel and apply electrical field to transport samples separated in first dimension to the second dimension.

The technique can be used for interfacing as many capillaries as desired, from at least 1 to ore than 1000 capillaries. The multiplexed capillary array electrophoresis (CAE) system contains an array of at least one (but possibly thousands) of capillaries, each preferably having an inside diameter of about 20–500 microns and a suitable outside diameter for the second dimension. Each capillary has an annular wall, an intake end, and an exit end. A more preferable inside diameter of each capillary is about 40–100 microns. The multiplexed CAE system may contain metal-coated capillary tips or metal tips glued to the capillary for better electric contact and better transfer of the samples from first dimension to the capillaries in the second dimension in CAE.

The present invention can be implemented utilizing an array of capillaries containing preferably at least about 1 capillary, and more preferably at least about 100 capillaries, and most preferably at least about 500 capillaries. A proper detector can be used to substantially monitor analyte separations by detecting the signals in a plurality of separation capillaries simultaneously. Inorganic materials such as quartz, glass, fused silica, and-organic materials such as Teflon™ and its related materials, polyfluoroethylene, aramide, nylon, polyvinyl chloride, polyvinyl fluoride, polystyrene, polyethylene and the like can be used. Proper seal is preferably placed between the capillaries to avoid buffer leakage.

This multiplexed CAE system can be used for analyzing macromolecules such as proteins, amino acids, polypeptides, carbohydrates, polysaccharides, oligonucleotides, nucleic acids, RNAs, DNAs, bacteria, viruses, chromosomes, genes, organelles, fragments, and combinations thereof. This invention is also equally applicable whether a gel is used in the CE system or not.

A method for transferring macromolecules, such as biological molecules, between two different electrophoresis steps using a multiplexing approach is also provided. According to this method, samples are introduced into capillaries of a capillary array in a CE system.

A first aspect of the present invention is a novel method for interfacing multi-dimensional capillary electrophoresis. The novelty of this interface lies in several areas. 1. This is the first system offering an interface between a capillary channel (with or without gel) electrophoresis to another capillary electrophoresis. 2. The two electrophoreses are interfaced perpendicularly. 3. The perpendicular interface allows selective transfer of samples separated in the first dimension to the second dimension. This selectivity allows sampling specific sample zone without waiting for all prior samples to be eluted first, as is in a series transfer from the end of the channel. This feature is especially important in saving the time when the electrophoresis is connected to other fast response detectors, such as MS. 4. This interface is the first in allowing the simultaneous interfacing of multiple capillaries in the second dimension to the channels in the first dimension. 5. This interface also allows the multiple capillaries fabricated on a microchip to be interfaced with the first dimension channels.

The second aspect of the present invention is to separate molecules in channels or capillaries for both dimensions simultaneously. This feature allows the automation of the whole process.

The foregoing and other objects and aspects of the present invention are explained in detail in the drawings herein and the specification set forth below.

BRIEF DESCRIPTION OF THE DRAWINGS

FIGS 1A and 1B are schematic diagrams for an IEF device using a channel fabricated on a polymer substrate with an IPG strip in the channel having features of the present invention. FIG. 1A is the top view. FIG. 1B is the side view of the device.

FIG. 2A is the top view of the channel on the substrate. FIG. 2B is the side view when the channel is fabricated on the surface. FIG. 2C is the side view when the channel is fabricated within the substrate. FIG. 2D shows an alternative design with the channel connected with external capillaries.

FIGS. 3B and 3C give the detail views of two different connection devices between a metal tubing tip and the capillary.

DETAILED DESCRIPTION OF THE INVENTION

Figures 2A, 2B, 2C, 2D:
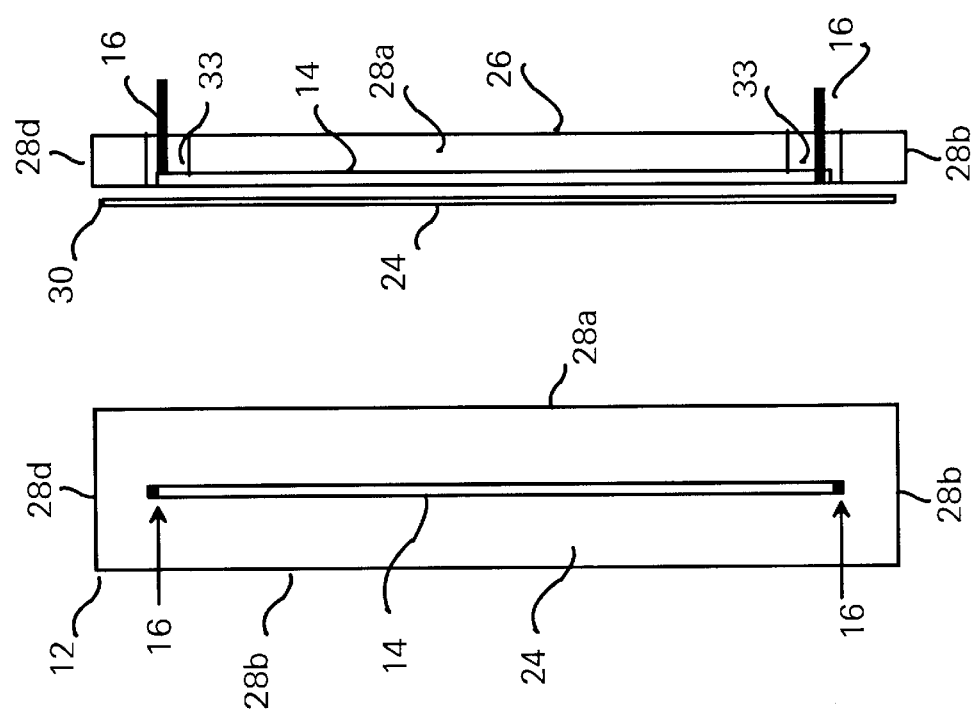
FIGS. 2A, 2B, 2C, and 2D are schematic diagrams for an IEF device using a channel fabricated on a polymer substrate without IPG strip (an open channel).

With reference to the figures, a two-dimensional capillary electrophoresis system 10 according to the present invention includes three major components. The first component is a planar device for running the first dimensional separation, such as IEF, in a miniaturized coplanar setting. Coplanar as used herein means lying or acting in the same plane. The planar device 20 according to the present invention includes a substrate 12 on a proper base 22 with at least one channel 14 plus a plurality of electrical conductors 16 at the ends to connect to power supply 21 for the electrophoresis. The second component is a multiple capillary device 40 for the second dimensional separation. The third component according to the current invention is an interface 18 designed for connecting the planar device to the multiple-capillary device 40.

THE PLANAR DEVICES

The heart of the planar device 20 is a substantially planar substrate 12 with at least one channel 14 disposed in it. The dimensions of the substrate 12 vary according to the desired design of the channel 14. The length of the substrate 12 is chosen based on the length of the channel 14 while the width of the substrate is based on the width and the number of the channel 14 on the substrate 12. The shape of the substrate 12 can be different including triangle, round, square and rectangular. In the embodiment shown in the figures, the substrate 12 is in rectangular shape.

The substrate 12 includes a top surface 24, an opposed bottom surface 26, and four side surfaces 28 including a front long side surface 28aa back long side surface 28b, a front short side surface 28c and a back short side surface 28d. The substrate 12 can be a piece of glass, plastic, semi-conductor, or other materials that is non-conductive to electricity and is feasible for fabricating channels 14 on it using current technologies, such as photolithographic or chemical itching (for glass), molding (for plastics), casting (for room temperature cure silicone rubber), and ablation, etc.

The substrate 12 can contain one or more channels 14. In the embodiments shown in FIGS. 1–4, the substrate 12 includes only one channel 14. In the embodiments shown in FIGS. 5–12 the substrate 12 includes multiple channels 14. Channel 14 can be an open channel when the width is less than 100 $\mu$m, which will form a capillary upon covering with a membrane cover 30. Typically, each of the open channels 14 has a cross-sectional area of between about one hundred to ten thousand square micrometers (100–10,000 $\mu m^2$). If necessary, higher viscosity including gel materials can be fed into the open channels 14 to enhance various separation needs. When the cross-sectional area of channel 14 is significantly larger (but less than 1×4 $mm^2$), channel 14 can also host a small IPG strip 32. FIG. 1 shows a planar device with a thin IPG strip inside the channel. FIG. 1A is the top view and FIG. 1B is the front long side view of the planar device 20. The IPG strip 32 is commercially available and can be cut into small pieces to fit the size of channel 14.

Normally, the commercial IPG strips 32 are about 4 mm wide and 1 mm thick with a cross-section area of 4 $mm^2$, which result in the operation current in the mA range under normal operation voltage. By cutting these IPG strips 32 to 1 mm or less, the operational current can be significantly reduced. For example, if a IPG gel strip of 100 $\mu m \times 1$ mm is used, a 40-fold reduction in current can be achieved. Lower current may tolerate the use of higher voltage for better separation and give higher efficiency. At the extreme, a capillary instead of the strip can be used. For example, if a 50-$\mu m$ capillary is used, 500 V/cm or higher electric field can be used without the concern for overheating. By reducing the size of channel 14 to capillary, it is also possible to run IEF without gel. This is a technique called capillary isoelectric focusing (cIEF), which is relatively fast and convenient.

Although capillary is super efficient in dispatching Joule heat, the amount of samples available for transferring to the next dimension will dictate how small the channel can be. Since samples separated from the first dimension need to be transferred to the second dimension for further separation, the first dimension has to be moderate size. At lease the channel 14 in the first dimension should be significantly larger than the internal diameter (ID) of the second dimension. Therefore, the normal range of the channel (or capillary) 14 should be in the range of 50 $\mu m$ to 4 mm. For the purpose of convenience, we will use "the channel 14" to represent the channel 14 even when the size of the channel has been reduced to capillary for the IEF dimension in the following context without differentiation.

Channel 14 can be fabricated either on the surface (FIG. 2B) or inside the substrate (FIG. 2C). When the channel 14 is fabricated on the surface only, a top cover 30 can be used to cover the surface channel to form a closed channel. The closed channel 14 can be an open tubular capillary (for the open channel embodiment) or a gel filled closed channel (for the channel with IPG strip 32). When the top surface 24 of the substrate 12 and the contacting surface of the top cover 30 are clean, they tend to seal very well to prevent the loss of buffer 34 in channel 14 due to evaporation.

The top cover 30 can be made of polymer materials. Usually, a silicone based polymer top cover 30 can be made by using the two parts room-temperature cure kits sold by Dow Corning of under the brand name Silgard® 184. These two components can be mixed well before use and cast into a mold to form the desired shape. The thickness of the top cover 30 can be controlled by the amount of materials used. Since mechanic strength is no an issue for top cover 30, which will lay on top of substrate 12, the top cover can be made in thin membrane for convenience of needle insertion as explained in details later.

Depending on the experimental design, proper patterns of some perforated small spots 31 can be made on the polymer membrane to facilitate the insertion by needles. These small spots 31 are perforated before the top cover 30 is attached to the substrate 12. These week spots 31 are usually small round circles with a diameter of 50–500 $\mu m$. When sealing to the top surface 24 of substrate 12, attention should be paid to align these perforated spots with the channels. This usually is easy as the channels 14 are generally larger than the small spots 31. The small spots 31 can also be used to serve another purpose of providing electric conductance for electric transfer of samples from channel 14 to the second dimensional separation as described in details below.

After covering with polymer membrane 30, each channel 14 can include at least one channel end opening 42. The channel end opening 42 extends either through an opening 33 located on the bottom surface of the substrate 12 (FIG. 2B) or through the connections 35 at the two short side surfaces 28b and 28d of substrate 12 to allow for connection to the electrodes 16 (FIG. 2D). In the embodiment shown in the FIG. 1 and FIGS. 2A–2B, the channel end openings 42 extend through the bottom side surface 26 of the substrate 12. Alternately, depending upon the design of the planar device 20, some or all of the the channel end openings 42 can extend through the any sides 28 of the substrate 12. In the embodiment shown in FIG. 2D), the capillary openings 42 extend through the front and back short sides 28b and 28d of the substrate 12.

Alternatively, depending on the experimental design, the two kinds of channel end openings 42 can be mixed together with one channel end opening 42 go through the bottom side surface 26 while the other channel end openings 42 go through the side surface 28. However, if more than one channel 14 is designed, all of the channel end openings 42 extending through the same surface 28 are preferably coplanar for convenience of fabrication.

Typically, each channel end opening 42 has a cross-sectional area and shape that is substantially equal to a cross-sectional area and shape of each channel 14. However, the size and shape of each channel end opening 42 can be larger or smaller depending upon the design of the channel end connection 35. In the embodiment shown in FIG. 1, the channel end opening 42 has a rectangular cross-sectional shape to facilitate the IPG strips. Alternately, the shape of the channel end opening 42 in FIG. 2 can have a circular cross-sectional or a square shape.

Figure 3B:
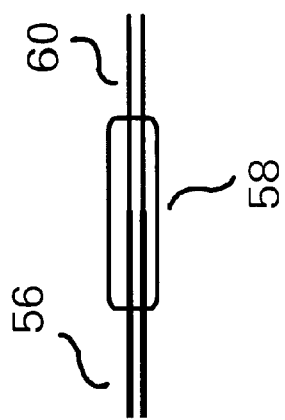
FIGS. 3A, 3B and 3C are schematic diagrams of the interface between the IEF channel with a strip and a single capillary (FIG. 3A).
Figure 3C:
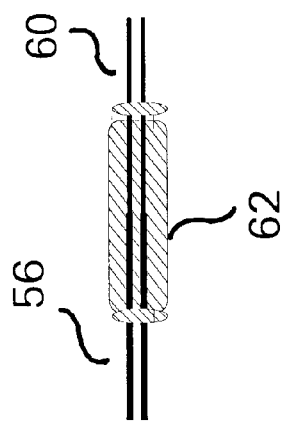
Figure 3A:
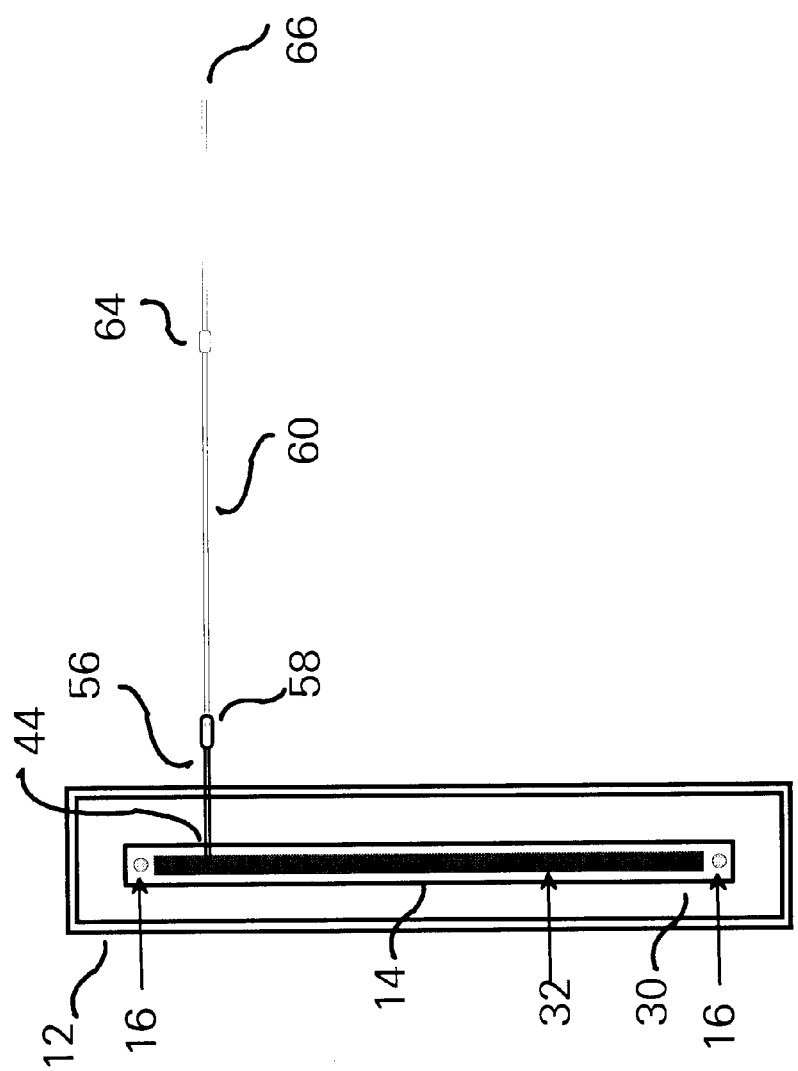
Figure 4:
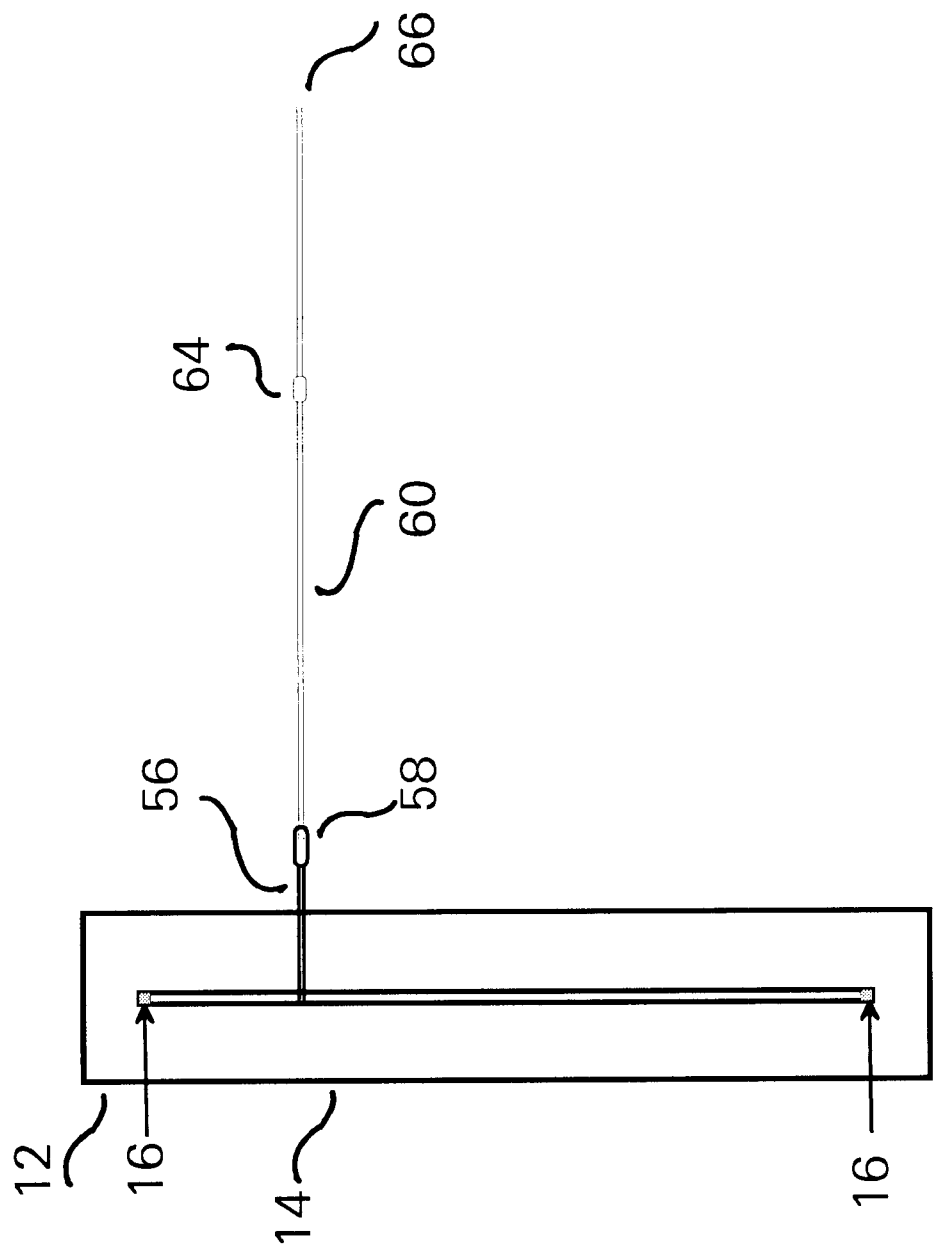
FIG. 4 is a schematic diagram of the interface between the IEF channel without gel strip (open capillary) and the capillary from the second dimension.

Depending on the design, channel 14 can also have side openings 44 (FIGS. 3–4). Preferably, these side openings 44 can be fabricated at the same time when channel 14 is fabricated. Alternatively, these side openings can be made after the fabrication of the channels 14 on the substrate 12. In the later case, these side openings have to be made on the rubber cover 30 with proper mold. The sizes and shapes of these openings 44 can very depending on specific designs. Preferably, the size of the openings 44 matches the cross-section sizes of the connecting capillaries. These opening can be directly connected to capillaries 60 of the second dimensional electrophoresis as described in details later.

Figure 10:
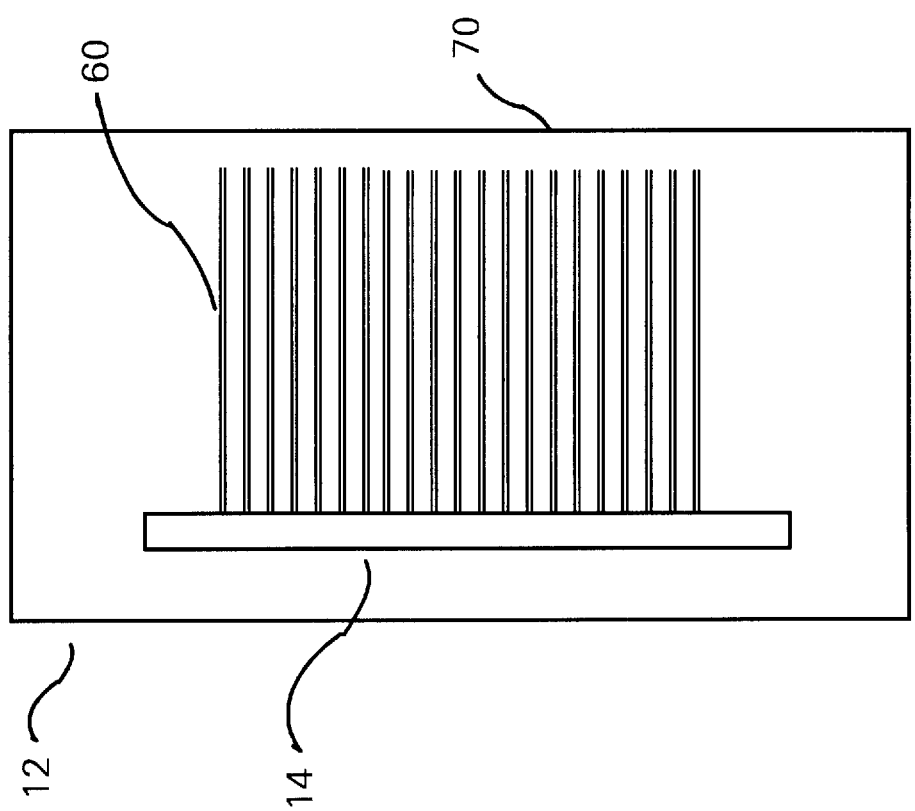
FIG. 10 shows the design of a single device containing both the IEF channel and the multiple capillaries.

The distance 46 between the centers of the adjacent openings is related to the openings and the outer diameters of the capillaries 60 for the individual capillary version (FIGS. 5–6) or the internal diameter of the capillary for the microchip version (FIG. 10). If all of the capillaries have the same outer diameter, the smallest possible distance 46 (FIG. 5) is the outer diameter of the capillaries. When the distance 46 is larger than the outer diameter of the capillaries, holes larger than the outer diameter of the capillary should be made to ensure the transfer of samples from the channel 14 to capillaries 60. In the embodiment shown in the figures, the side openings 44 are evenly spaced with proper distance 46. Depending on the design, other arrangement of the distance 46 as well as the shape of the side opening can be fabricated.

Two platinum electrodes 16 for each channel 14 are placed in reservoirs 36 near the ends of the IPG strip 32 (FIGS. 1 and 3). The electrodes 16 are connected to power supply 21 to provide a driving force to move the liquid in channel 14. The channel 14 can be limited length with the electrodes 16 attached to the end of the channel 14 on the substrate 12 (FIGS. 2A–2C) or connected with connecting capillaries 50 (FIG. 2D) for easier operation of sampling and automation. Reservoirs 36 provide the source of liquid supply with the channel 14. The connecting capillaries 50 serve the purpose of liquid communication connecting with outside reservoirs (not shown), where two electrodes 16 are connected to power supply 21 to form a closed electric circuit. This design of a close loop forms an independent capillary electrophoresis system.

MULTIPLE CAPILLARY DEVICE

Referring to FIGS. 3–12, a multiple capillary device 40 consists of at least one capillary and preferably hundreds of capillaries 60, a power supply 54, a polarity of electrodes 16, a buffer reservoir at the outlet end 66, and a detector 48. The said capillaries 60 have one inlet end 65 and an outlet end 66 for each capillary 60. The said inlet end 65 and outlet end 66 can be placed into reservoirs 36, where electrodes 16 connecting to power supply 54 can be placed in to form a closed loop of electric communication between the power supply 54 and the capillaries 60. The said reservoirs 36 provide liquid communication with the multiple capillaries 60. Alternatively, the said inlet end 65 of the capillaries 60 can be placed in connection with the planar device 20 described before. The details for the interface will be described later.

The said detector 48 can be any of the conventional detectors used for capillary electrophoresis, such as UV-Vis, laser induced fluorescence, electrochemical, and MS detectors. When more than one capillary 60 is used, the detector has to be modified to accommodate the needs. In general, there are two detection schemes, one is to detect one capillary at a time and the other is to detect all of the capillaries simultaneously. The details of both methods are well documented in references (Kheterpal, I. and Mathies, R. A., *Anal. Chem. News and Features*, Jan. 1, 1999, 31A–37A). Mathies et al. used a rotary confocal scanning method to detect one capillary at a time (Mathies, R. A. and Huang, X. C., *Nature (London)* 1992, 359, 167–169). There are three different ways of achieving simultaneous detection of all capillaries. (1) Ueno et al. used on-column line-focusing detection method (Ueno, K. and Yeung, E. S., *Anal. Chem*, 1994, 66, 1424–31). (2) Takahashi, et al. described a multiple-sheath flow detection (Takahashi, S., Murakami, K., Anazawa, T., and Kambara, H., *Anal. Chem.* 1994, 66, 1021–26). (3) Quesada, et al. used fiber-optic array to split the incident light into multiple beams onto the capillaries and detected the images of all the capillaries simultaneously by a charge coupled device (CCD) camera (Quesada, M. A. and Zhang, S., *Electrophoresis*, 1996, 17, 1841–51). Any of these detection schemes can be adopted as the detection method for this multiple capillary device 40.

Alternatively, MS detector can be used as a detection method for the multiple capillary device 40. Since MS is a serial detector, it can detect only one sample at a time. Another interface is needed to connect MS detector the multiple capillary device 40. The other option is to bundle the outlet end 66 of capillaries 60 into a specific geometry and in contact with the sampling plate of a MALDI-TOF MS for detection.

THE INTERFACE

The interface describes the actual method of transferring samples from the first dimension, i.e. the planar device 20, to the multiple-capillary device 40 in the second dimension. For different format of the multiple-capillary device 40, i.e. single capillary, multiple capillary and microchip, there are different ways of interfacing these two dimensions.

In general, samples from the planar device 20 can be transferred to the multiple-capillary device 40 by either hydrodynamic or electrokinetic process. If the first dimensional separation is accomplished in an open capillary, a vacuum can be applied to the outlet end 66 of the capillaries 60 to introduce samples to the second dimension. Alternatively, an electrical potential across the capillary 60 will also facilitate the transfer of samples to capillaries 60. If IPG gel strip is used in the planar device 20, only electrokinetic process can be used to transfer samples to capillaries 60.

There are four ways to physically connect the capillaries 60 to the planar device 20. First, capillaries 60 are totally separated from the planar device 20. The connection happens only when the inlet ends 65 of capillaries 60 are in contact with channel 14 through either pre-drilled side openings 44 on the substrate 12 or through insertion into the perforated small spots described earlier. The side openings 44 can also be formed during fabrication process. Second, the inlet ends 65 of the capillaries 60 can be temporarily glued to substrate 12 and are in contact with channel 14. When sample transfer process is complete, these capillary ends can be pulled out and placed into reservoirs to start the electrophoresis process of the second dimension. Third, the inlet ends 65 of the capillaries 60 can be permanently mounted onto to substrate 12 and are in contact with channel 14. The channel may serve as a reservoir after sample transfer. Finally, the inlet ends 65 of capillaries 60 can be fabricated on a single substrate as microchip. The connection between capillaries 60 and channel 14 is fixed on the microchip.

Referring to FIGS. 3–12, the interface between capillaries 60 and channel 14 can be accomplished in the following ways:

A. SINGLE CAPILLARY INTERFACE

A single capillary 60 represents the simplest interface to channel 14 (with or without the gel). Referring to FIG. 3A, the channel 14 with a gel strip 32 in the first dimension and a single capillary 60 in the second dimension is connected through the site opening 44. Although optional, a metal tubing tip 56 may be used to facilitate the connection. This metal tubing tip 56 can be attached to the end of the capillary 60 by either gluing their ends together in a connection tube 58 (FIG. 3B) or through a union 62 (FIG. 3C). The connection tube 58 can be a peek tubing or a metal tubing with an internal diameter slightly larger than the outside diameter of the capillary 60 and the metal tubing tip 56. A union 62 such as Upchurch P-720 can also be used to join the metal tubing tip 56 and the capillary 60.

FIG. 4 shows the interface between the channel 14 without gel (capillary) and a capillary 60 through metal tubing tip 56. The IEF Channel 14 has a larger diameter than capillary 60. With the help of a positioning device, the metal tubing tip 56 can pin into any position on channel 14 to transfer samples.

The metal tubing tip 56 serves multiple functions. The first function is to serve as a carrying tube to transport the samples from channel 14 (with or without gel) to capillary 60. For this purpose, the use of the metal tip is optional. The second function of the metal tubing tip 56 is to serve as a needle to punch through the weak small spots 31 perforated on top cover 30. If bare silica capillary 60 alone is used to directly transfer samples from the IEF channel 14, the cover may have to be removed or have to have pre-drilled holes. Either situation will not be desirable and risk to loss samples due to the extremely small sample volume involved.

The third function of the metal tubing tip 56 is to serve as an electrode to conduct electricity from the second power supply 54 to capillary 60. There are at least two advantages of using the metal tip 56 as an electrode. First, the metal tubing tip 56 avoids the bias associated electrokinetic sampling process because of charges difference on different analytes. The metal tubing provides a segment of constant voltage for the capillary and both positive and negative analytes will be transferred into the capillary at the same speed. Second, by using the metal tubing tip 56 as the electrode, it is possible to apply the high potential directly onto the individual inlet end 65 of capillary 60. This will avoid diffusion and move of the sample bands resulted from by the first dimension separation into wrong capillary tubing 60 during the sample transferring process.

A detection window 64 can be opened on the capillary to facilitate the on-column detection (FIG. 4). The outlet 66 of the capillary 60 can be used for interfacing with other detectors, such as MS as well as providing electric connection to the power supply 54.

B. MULTIPLE CAPILLARY INTERFACE

Figure 5:
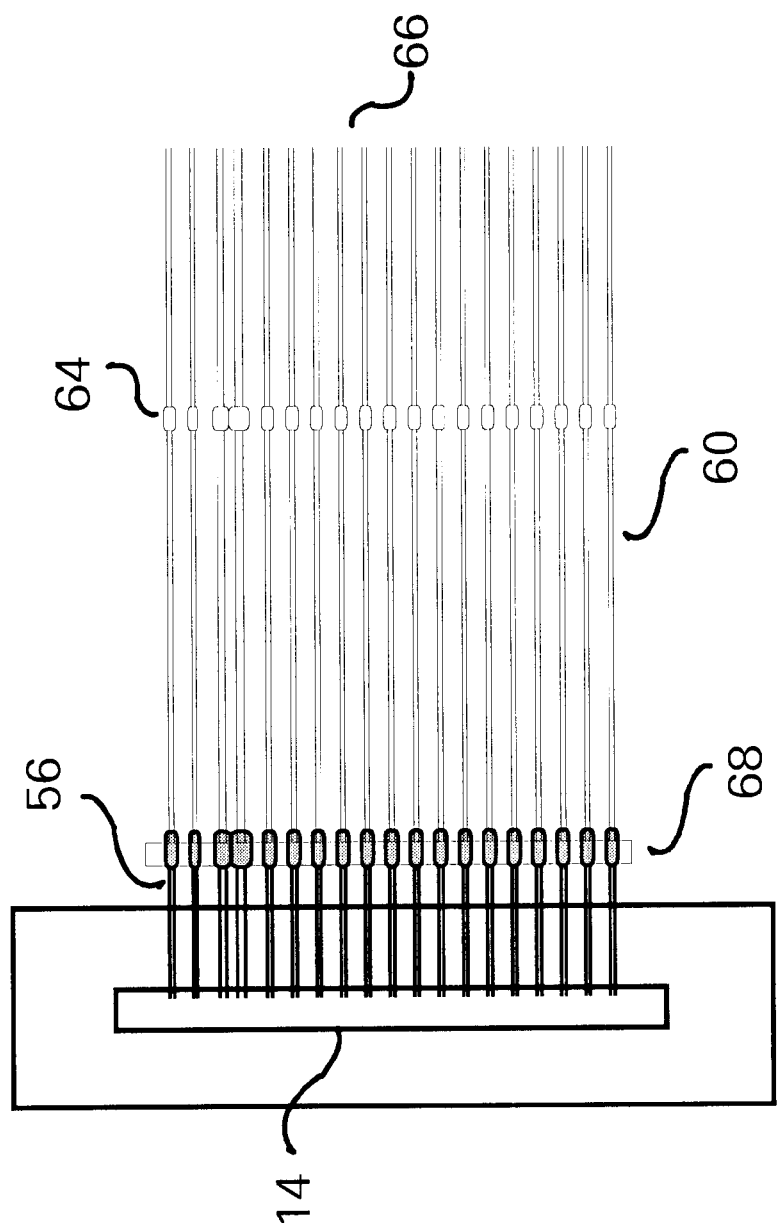
FIG. 5 is a schematic diagram of the interfaces between either a single IEF strip (a) or a single channel (b) and the multiple capillaries in second dimension.
Figure 6:
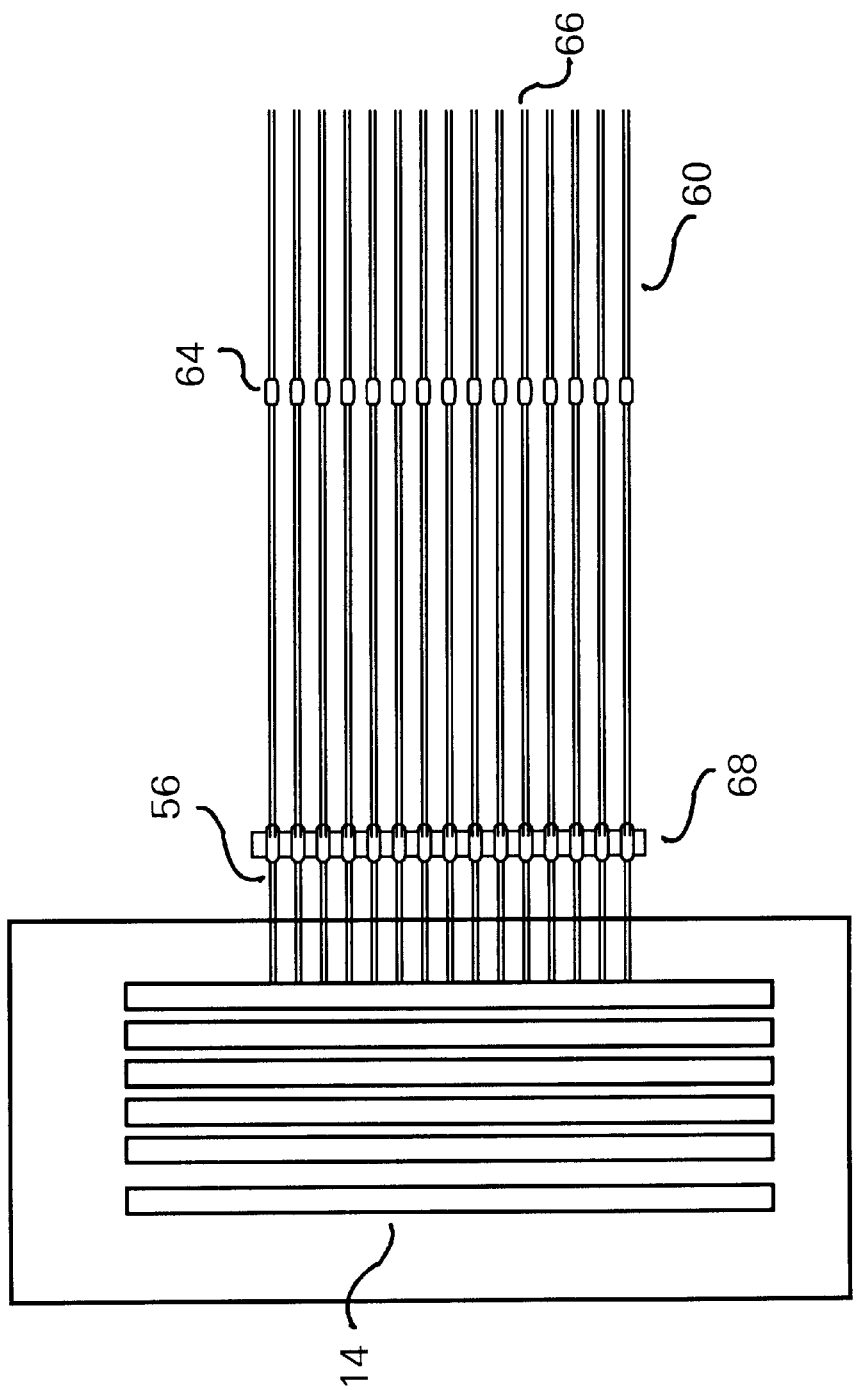
FIG. 6 is a schematic diagram of the interfaces between multiple IEF channels and multiple capillaries in the second dimension with all the capillaries sampling from a single channel simultaneously.
Figure 7:
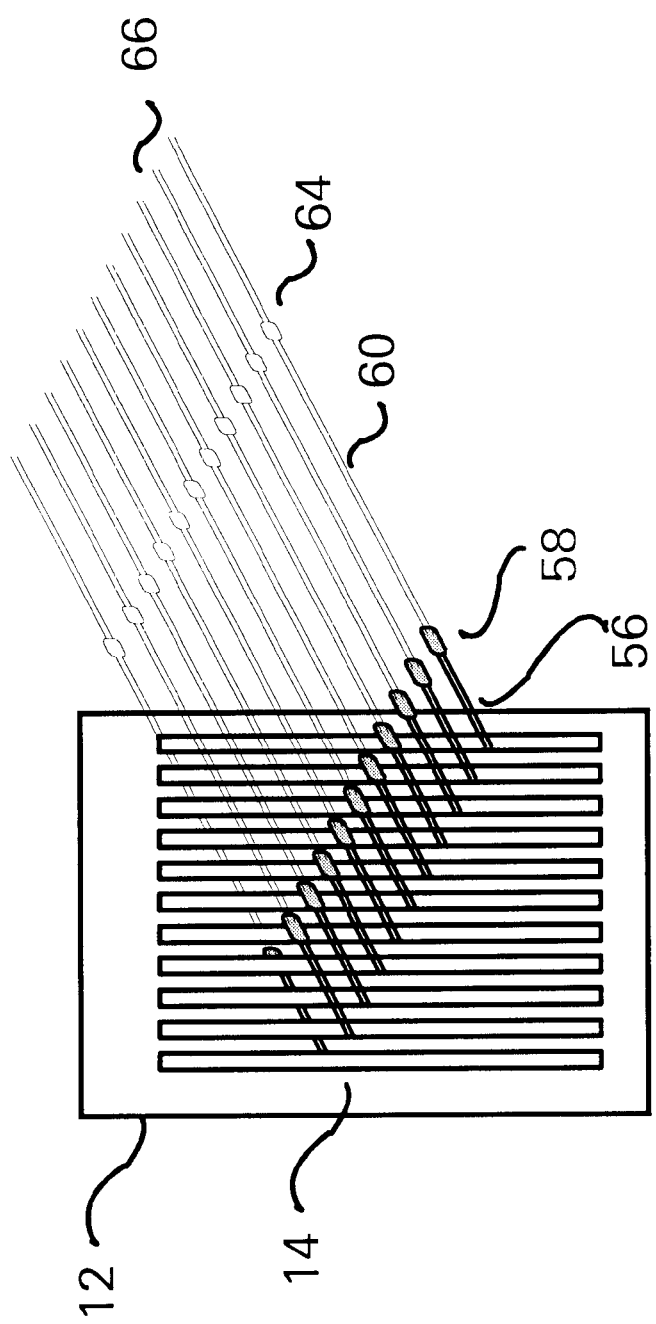
FIG. 7 is a schematic diagram of the interface between multiple IEF channels and multiple capillaries with all the capillaries sampling from different channels.
Figure 8:
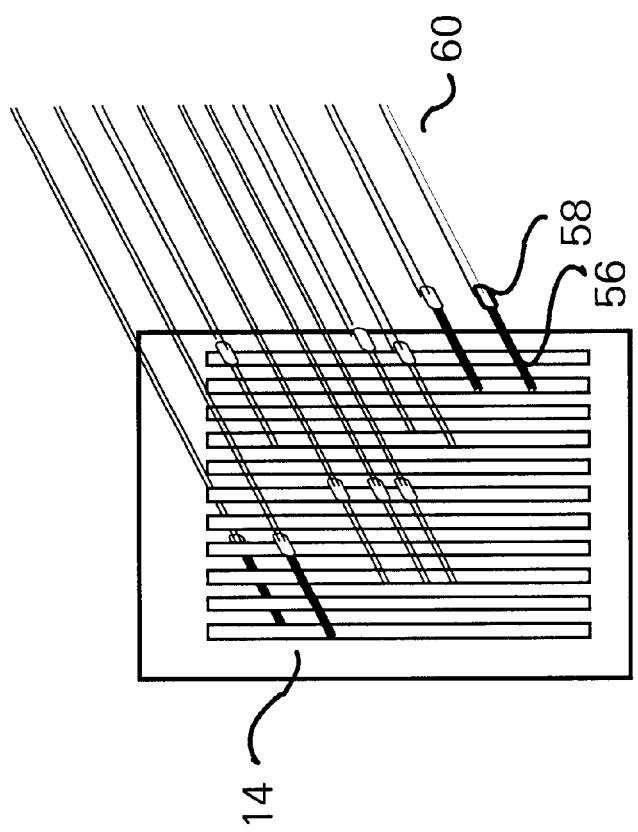
FIG. 8 is a schematic diagram of the interface between multiple IEF channels and multiple capillaries with the capillaries sampling randomly from different channels.

In addition to the single capillary interface as shown in FIGS. 34, it is also possible to sample multiple points simultaneously by using multiple capillaries 60 from the multiple-capillary device 40 (FIGS. 5–6). Further, if the first dimension contains multiple channels 14, more options are available for interfacing the multiple capillaries 60 with channels 14 (FIGS. 7–8).

When interfacing to a single channel 14, all or part of the multiple capillaries 60 may be used simultaneously. FIG. 5 shows the interface s between the channel 14 and multiple capillaries 60. The details of the interfaces between each of the capillaries 60 and the IEF strip 32 and the channel 14 are similar to that described in FIG. 3 and FIG. 4, respectively. These outlet ends of capillaries 60 can be bundled together for easy on-line detection. The inlet ends 65 of capillaries 60 can be either individually controlled for maximum flexibility or bundled together through a capillary holder 68. This capillary holder 68 can control the capillaries 60 as a whole for easy movement. The capillary holder also allows the movement of each individual capillary 60 for easy access to random positions (FIGS. 7–8). With proper wiring, the capillary holder 68 can also serve as a common grounding point for the inlet ends 56 during the electrophoresis process. The outlet 66 of these capillaries 60 can be in a common reservoir (not shown) or controlled individually.

When there are multiple channels 14 are involved for the first dimension separation, there are three different ways of making the interfaces between the multiple channels 14 and the capillaries 60. First, all or some of the multiple capillaries 60 can interface with one single channel 14 at a time (FIG. 6). This is very similar to the single channel 14 situation described above. Secondly, multiple capillaries 60 can sample from the same number of different channels 14 simultaneously (FIG. 7). The voltage applied onto the channels 14 can be controlled for individual channels. This design allows repeat of multiple samples simultaneously.

The third interface between multiple channels 14 and capillaries 60 is a random connection. FIG. 8 shows the interfaces between multiple channels 14 and the multiple capillaries 60 in a random fashion. The randomness of this interface lies in two folds. First, the number of capillaries 60 on a specific channel 14 is randomly determined based on specific needs. Second, the capillaries 60 are randomly connected to different positions on the channels 14. Each of the capillaries 60 can be controlled individually for easy maneuver. This offers the maximum freedom and flexibility for connection. It offers the potential of eliminating unnecessary repetitive work by sampling only these positions of interests

C. MICROCHIP INTERFACE

Figures 9A, 9B:
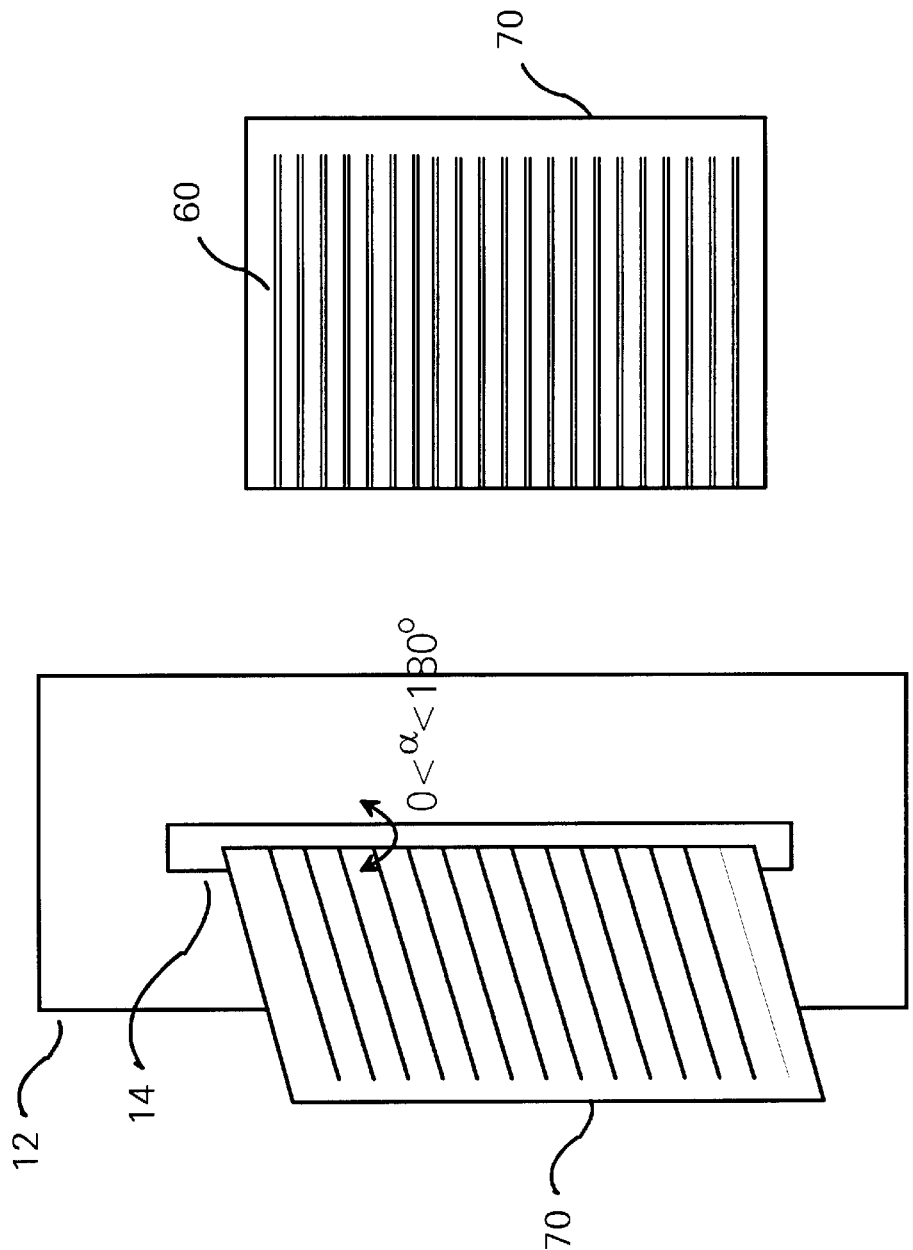
FIGS. 9A and 9B are schematic diagrams of the interface between either an IEF channel and multiple capillaries fabricated on a microchip.
Figure 11:
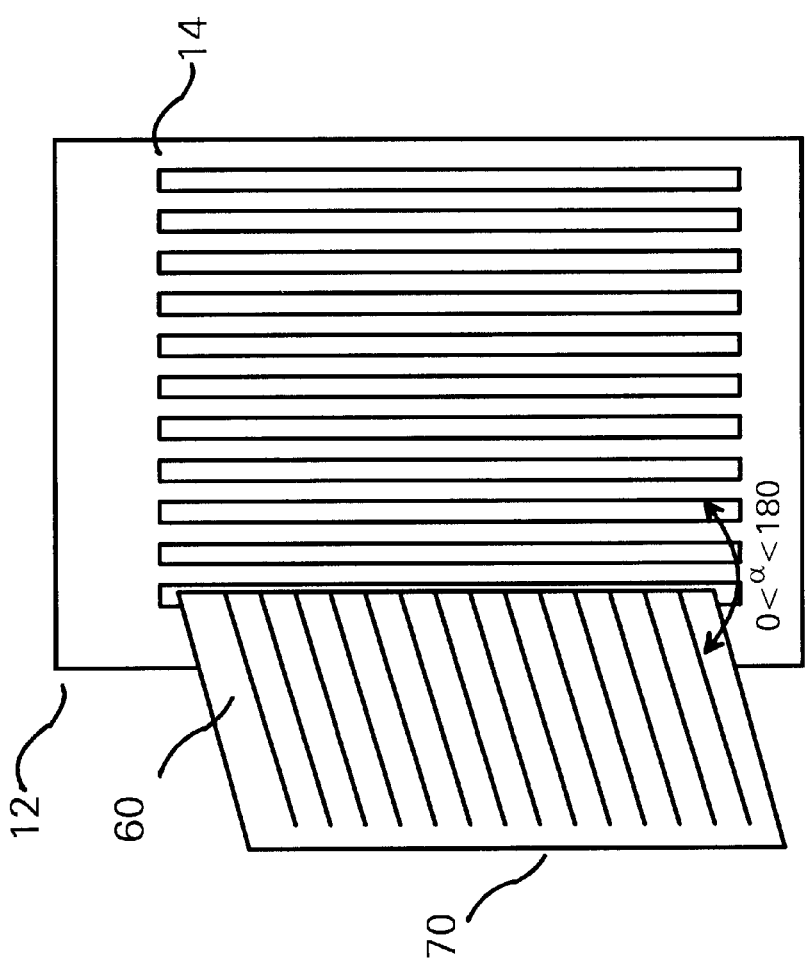
FIG. 11 is a schematic diagram showing the interface between multiple IEF channels and multiple capillaries fabricated on a microchip with all the capillaries connected to a single IEF channel.
Figure 12:
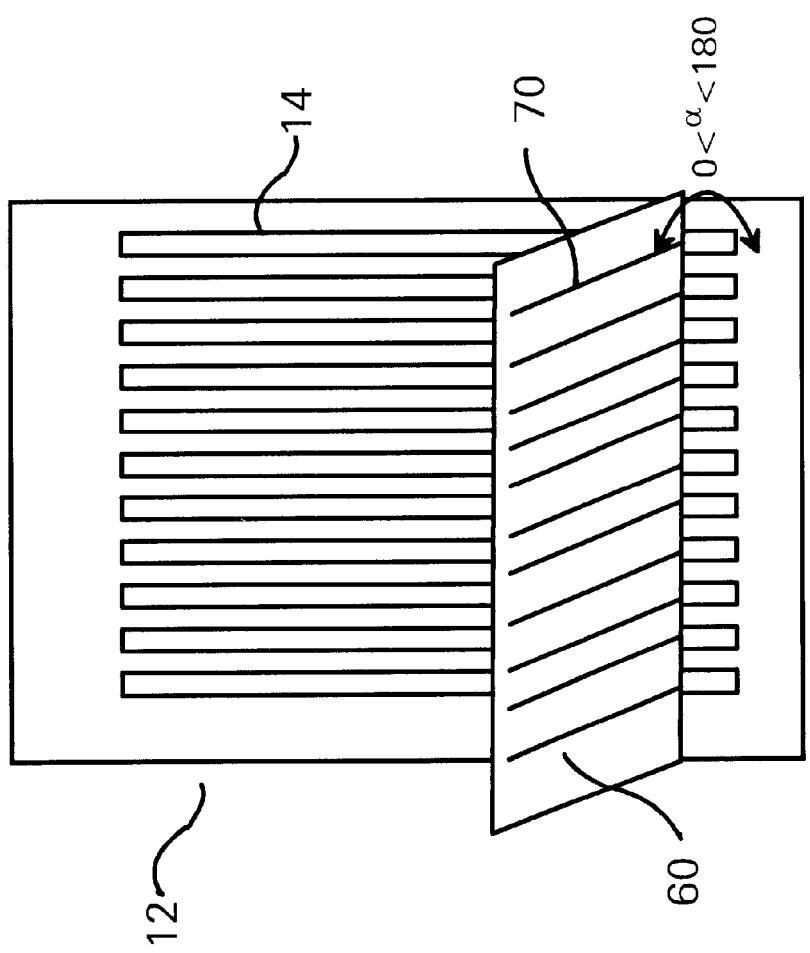
FIG. 12 is a schematic diagram showing the interface between multiple IEF channels and multiple capillaries fabricated on a microchip with the capillaries connected to multiple IEF channels.

For convenience, both the multiple channels 14 and multiple capillaries 60 can be fabricated on microchips 70 (FIGS. 9–12). Microchip fabrication will allow the size of the channels 14 to be reduced to the micrometer range. However, as discussed earlier, the requirement for available sample amount eliminates the usefulness of extremely small channels. Therefore, the channels 14 associated with this invention will be in the range from 50 $\mu$m to 4 mm. This can be easily fabricated with conventional casting method for polymers when proper mold is available. If capillaries 60 for the second dimension are fabricated on a microchip, the mechanic strength of the microchip should be high enough to provide connection with channels 14 on substrate 12. Preferred materials are glass and plastics, which can be fabricated using photolithography or ablation process. Thus, the microchip containing capillaries 60 can be interfaced with the channels 14 in substrate 12 (FIG. 9). Since the microchip 70 is a fixed object, it is relatively easy to handle all of the capillaries 60 together. However, it does not have the flexibility of controlling individual channels from the edges. Therefore, only two kinds of interfaces are possible for a single channel 14 (FIGS. 9–10). One is to interface the capillaries 60 on the microchip to a single channel 14 through either out of the plane (FIG. 9) or in the same plane (FIG. 10). When multiple channels 14 are involved, a third way of interfacing the capillaries with the channels is available (FIG. 12).

FIG. 9 shows the interface of a single channel 14 to a microchip 70 containing multiple capillaries 60. Special fabrication process is needed to generate needles along the interfacing side 72 of the microchip 70. These needles will penetrate the thin membrane of the week small spots 31 to create connection with channels 14. Alternatively, the top cover 30 on the substrate 12 can be removed before the microchip 70 is attached to the channels 14. This connection is especially feasible when gel is used in channels 14.

The multiple capillaries 60 can also be fabricated on the substrate 12. These multiple capillaries 60 are coplanar and perpendicular to channels 14 (FIG. 10). This is a miniaturized version of the conventional two-dimensional gel.

If multiple channels 14 are involved, the multiple capillaries 60 on a microchip 70 can interface with the multiple channels 14 by either one channel at a time or multiple channels simultaneously. FIG. 11 shows the interface between multiple channels 14 and multiple capillaries 60 fabricated on a microchip 70 with all the capillaries 14 connected to one single channel. FIG. 12 indicates that the capillaries 60 on the microchip 70 can interface with different channels 14 of the multiple channels 14 simultaneously. Depending on the relative distance between the channels 14 and the capillaries 60, it is possible to have more than one capillaries interfaced with a single channel at the same position. This is potentially advantageous because it allows multiple sampling from the single sample point (FIG. 12).

APPLICATIONS

Until very recently protein science has been a slow and frustrating art. Unlike the development of DNA sequencing and mRNA screening, where literately thousands of genes can be rapidly analyzed in a well-equipped laboratory, the purification and characterization of a single protein takes a lot more effort. However, the dramatic changes in proteomics have been converging in protein science and bioinformatics to produce the revolution that allows proteins, like DNA and mRNA, to be subject to mass screening.

Protein technology is inherently more complex than DNA-based technology. Not only is the basic alphabet bigger (4 nucleotides for DNA vs. 20 unmodified and many more modified amino acids for proteins), but some genes can be variously spliced therefore making numerously different proteins from a single stretch of DNA. Additionally, mRNA editing is relatively common, leading to modified messages and corresponding protein products. There are also many ways in which proteins are modified after they have been synthesized. To make matters still more complicated, while an organism has effectively a single genome, there are many proteomes. Even in a unicellular organism, the expressed proteins (proteome) will be different depending on the growth conditions.

The technologies required to separate large numbers of proteins in a proteome, to identify them, and to study their modifications are by no means straightforward. However, many technologies are converging and making proteome analysis possible. The best techniques suited for proteomics today include sample preparation, two-dimensional gel electrophoresis, post separation analysis (imaging, mass spectrometry), and bioinformatics. At the heart of the technologies for proteomics is the 2-D gel electrophoresis. The separation of proteins is a pre-condition for the identification, modification and characterization of these proteins using the subsequent techniques. Using 2-D electrophoresis, individual proteins can be separated, identified, and characterized though a slow and tedious process. Benefited from the massive databases of inferred protein sequence established by DNA sequencing initiatives, protein identification in the genome era is easier than it was in earlier times.

The new device associated with the current invention revolutionizes the current practice of the 2-D electrophoresis by combining multiple steps and several instruments into one single process. The complete system based on this invention will enable the automation of the currently tedious 2-D electrophoresis procedures. The system will be a turn-key system to allow novice and casual users to perform the separation and quantitation of proteins on-line simultaneously with high accuracy and precision. This device will also enable the quantitation of the proteins on-line without the time consuming and tedious staining process.

Being able to quantitate proteins is critical because the emphasis of many biological researches has gone from a focus on protein identification to protein characterization. Already we are not content just to know the identity of a protein. We want to know how much of the protein is present in the cell. Further, we are not satisfied with the information on what proteins are. We want to know much more. With the rapid development in other analytical techniques, such as computer imaging and mass spectrometry, all of these are becoming possible on picomole amounts of proteins. Unfortunately, 2-D slab gel electrophoresis is becoming the major limiting step in the whole process of answering these questions.

The most obvious and important limitation of the current 2-D PAGE is poor quantitation. From a practical point of view, most physiological and pathological processes are associated with quantitative variation in the amounts of gene products. The most widely used techniques to detect protein spots on gels are silver staining and Coomassie Blue staining. Neither of these detection methods is very quantitative. They are far from stoichiometric and need protein specific staining density vs. protein concentration curves, which are often hard to obtain. They have uneven staining density at saturated spots and have low linearity ranges (40–50 fold ranging from 0.04 to 2 $ng/mm^2$ for silver staining and 20 fold ranging from 10 to 200 $ng/mm^2$ for Coomassie Blue staining). The overlap between protein spots make it extremely difficult to quantitate proteins in the "crowded" area. All of above difficulties with protein staining remain to be challenges to protein quantitation. These challenges must be solved before 2-D PAGE databases can be extended to consider protein abundance as components of pathological responses.

The current 2-D PAGE is also difficult to interface with other technologies. The 2-D PAGE takes several hours to complete and has to be done in separate steps. The results have to be visually examined first and comparisons are made manually before a decision can be made on which protein spot on the gel should be sequenced. This makes it very difficult for other instruments, such as MS, to be interfaced on-line with 2-D PAGE.

Another limitation of the current 2-D PAGE is its complexity. In the eyes of many researchers who are not "in the field", 2-D PAGE is still yet to become a routine separation vehicle.

All of the aforementioned limitations can be eliminated if the proteins separated by the 2-D PAGE can be easily transferred from the SDS slab gels into a different system more suitable for detection. Therefore, the key to overcome the current limitations in 2-D PAGE is to find a way of transferring the separated proteins into a different format for easier detection.

By running the first dimension in a channel (or capillary) and interfacing it to one or more capillaries in the second dimension, this current invention solves many of the limitations associated with 2-D PAGE by offering several advantages.

First, by transferring the proteins from the channels to capillaries, this invention allows the detection and quantitation of proteins directly on-line without any staining steps.

The current invention uses electrophoresis to transfer samples between the first and the second dimensions. This is the most efficient means of transferring samples among all known methods.

In addition to less Joule heat and higher efficiency, running electrophoresis in channels (0.1×1 to 2×1 $mm^2$) or capillary (25–100 $\mu$m internal diameter) instead of slab gel also eliminates the diffusion of protein bands in direction perpendicular to the electric field. The reduced dimension also requires much less protein samples for analysis.

The current invention enable us to make a new complete instrument system that can be fully automated for continued analysis of biopolymers. This automated instrument can perform sample application and on-line detection. It is easy to connect with MS or other instruments to make the whole analysis of protein identification, characterization and quantitation process into a single on-line system.

Since the experimental results obtained from the current invention contain the same information, i.e. the pIs and molecular weights as obtained from 2D-PAGE. These results can be compared directly with the 2-D PAGE protein databases currently available. In addition, the quantitative information generated by this technique may be added to the current database and make it more useful.

The miniaturized channels and capillaries will allow different modes of separations, such as capillary zone electrophoresis, to be run on this system. Therefore, this system is significantly versatile when compared with the current 2-D PAGE system.

All publications and patent applications cited in this specification are here in incorporated by reference as if each individual publication or patent application were specifically and individually indicate to be incorporated by reference.

Although the forgoing invention has described in considerable details for clarity of understanding, it will be readily apparent to those of ordinary skill in the art in light of the teachings of this invention that certain changes and modifications may be made thereto without departing from the spirit of or scope of the appended claims. Therefore, the spirit and scope of the appended claims should not be limited to the description of those preferred versions that are contained herein.

Other embodiments are within the following claims. We claim:

1. A system for performing two-dimensional electrophoresis, comprising:
    a first electrophoresis device having
        a first cathode,
        a first anode,
        a substrate having a top surface, a bottom surface, side surfaces, and at least one channel disposed within the substrate for transporting fluid during electrophoresis, and
        a substantially planar top cover on the top surface of the substrate to a sealed channel in the substrate; and
    a second electrophoresis device having
        a second cathode,
        a second anode,
        a buffer reservoir, and
        a plurality of capillaries, each of the capillaries having a longitudinal axis which is positioned angularly relative to the direction of electric current flow from the anode to the cathode of the first electrophoresis device, a proximal end capable of being electrically coupled to the channel within the substrate, and a distal end in contact with the buffer reservoir of the second electrophoresis device,
    wherein the planar top cover is aligned to be coplanar with the substrate of the first electrophoresis device and contains perforated openings for access of the capillaries to the sealed channel.

2. The system of claim 1, wherein the substrate is made of electrically non-conductive material selected from the group consisting of glass, plastics and rubber.

3. The system of claim 1, wherein the channel has openings extending through the top, side or bottom surface of the substrate to form fluid communication.

4. The system of claim 1, wherein the shape of the channel is circular, rectangular or square.

5. The system of claim 1, wherein the channel has a substantially constant cross-sectional area throughout the length of the channel.

6. The system of claim 1, wherein the substrate has more than 2 channels, each of which is fabricated on the same substrate.

7. The system of claim 1, wherein the top cover is made of polymer material.

8. The system of claim 1, wherein the perforate openings are circles with a diameter of 50 to 500 micrometers.

9. The system of claim 1, wherein the capillaries are coupled to the channel by pinching through the top cover.

10. The system of claim 1, wherein the channel contains an aqueous medium without a gel inside.

11. The system of claim 1, wherein the channel contains an aqueous medium with a gel inside.

12. The system of claim 3, wherein the substrate further has a plurality of channel openings on the side surfaces of the substrate to allow access of the capillaries to the channel.

13. The system of claim 12, wherein the channel openings are arranged side-by-side in parallel.

14. The system of claim 12, wherein the channel openings are scattered and separated with different distance from each other.

15. The system of claim 1, wherein the proximal end of each of the capillaries is in direct fluidic communication with the channel.

16. The system of claim 1, wherein the proximal end of each of the capillaries is coupled to the channel via a metal tubing tip coupled to the proximal end or to the substrate.

17. The system of claim 16, wherein the metal tubing tip is made of electrically conductive material having sufficient mechanic strength for accessing the channel.

18. The system of claim 17, wherein the metal tip is made of platinum.

19. The system of claim 16, wherein the metal tip serves as the second cathode or anode of the second electrophoresis device.

20. The system of claim 16, wherein the metal tip is configured in a needle shape for pinching through the top cover to establish fluidic communication between the capillaries and the channel.

21. The system of claim 16, wherein the metal tip is coupled to the proximal end of each of the capillaries through a union.

22. The system of claim 16, wherein the metal tip is coupled to the proximal end of each of the capillaries in a connection tube.

23. The system of claim 1, wherein the proximal end of each of the capillaries is coupled to the channel via a metal capillary holder that holds the capillaries and positions the proximal end for access to the channel.

24. The system of claim 1, wherein the capillaries are made of an electrically non-conductive material.

25. The system of claim 24, wherein the electrically non-conductive material is selected from the group consisting of fused silica, quartz, inorganic polymers, and organic polymers.

26. The system of claim 1, wherein the capillaries are arranged in an array.

27. The system of claim 26, wherein the capillaries are arranged side-by-side in parallel or scattered and separated with different distance from each other.

28. The system of claim 1, wherein the distal ends of the capillaries are in electric contact with the same second anode or cathode.

29. The system of claim 1, wherein each of the distal ends of the capillaries is in electric contact with a separate second anode or cathode.

30. A system for performing two-dimensional electrophoresis, comprising:
    a first electrophoresis device having
        a first cathode, a first anode, a substrate having a top surface, a bottom surface, side surfaces, and at least one channel disposed within the substrate, the channel being adapted for transporting fluid during electrophoresis, and a substantially planar top cover on the top surface of the substrate to form a sealed channel in the substrate; and a second electrophoresis device having a second cathode, a second anode, a buffer reservoir, and a plurality of capillaries, each of the capillaries having a longitudinal axis which is positioned angularly relative to the direction of electric current flow from the anode to the cathode of the first electrophoresis device, a proximal end coupled to the sealed channel within the substrate via a metal tubing tip configured for pinching through the top cover to establish fluidic communication between the capillaries and the channel, and a distal end in contact with the buffer reservoir of the second electrophoresis device.

* * * * *